(12) United States Patent
Chung et al.

(10) Patent No.: US 10,383,508 B2
(45) Date of Patent: Aug. 20, 2019

(54) ENDOSCOPE, HANDPIECE OF ENDOSCOPE, CALIBRATION METHOD THEREFOR, AND METHOD FOR USING THE SAME

(71) Applicants: GWANGJU INSTITUTE OF SCIENCE AND TECHNOLOGY, Gwangju (KR); KOREA UNIVERSITY RESEARCH AND BUSINESS FOUNDATION, Seoul (KR)

(72) Inventors: Euiheon Chung, Gwangju (KR); Wonshik Choi, Seoul (KR); Changhyeong Yoon, Seoul (KR)

(73) Assignees: GWANGJU INSTITUTE OF SCIENCE AND TECHNOLOGY, Gwangju (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 731 days.

(21) Appl. No.: 14/627,067

(22) Filed: Feb. 20, 2015

(65) Prior Publication Data
US 2016/0242633 A1     Aug. 25, 2016

(51) Int. Cl.
*A61B 1/00* (2006.01)

(52) U.S. Cl.
CPC ...... *A61B 1/00172* (2013.01); *A61B 1/00009* (2013.01); *A61B 1/00057* (2013.01); *A61B 1/00165* (2013.01)

(58) Field of Classification Search
CPC ........................... A61B 5/0066; A61B 5/0084

USPC .................................. 600/160; 356/477, 497
See application file for complete search history.

(56) References Cited

U.S. PATENT DOCUMENTS

| 5,716,324 | A | * | 2/1998 | Toida | .................. | A61B 5/0084 356/484 |
| 2006/0215975 | A1 | * | 9/2006 | Kim | .................. | G01M 11/3172 385/123 |
| 2008/0192236 | A1 | * | 8/2008 | Smith | .................... | A61B 1/303 356/73 |
| 2012/0026503 | A1 | * | 2/2012 | Lewandowski | .... | G01N 21/4795 356/477 |
| 2012/0188538 | A1 | * | 7/2012 | Patil | ...................... | A61B 3/102 356/301 |

(Continued)

FOREIGN PATENT DOCUMENTS

| JP | 05115467 A | 5/1993 |
| KR | 20040065178 A | 7/2004 |
| KR | 20130080940 A | 7/2013 |

*Primary Examiner* — Alexandra L Newton
*Assistant Examiner* — Rynae Boler
(74) *Attorney, Agent, or Firm* — Hauptman Ham, LLP

(57) ABSTRACT

Provided is an endoscope including a hand piece held by a hand and a main body connected to the hand piece. The hand piece may include a high-strength bar having an optical path providing unit formed therein, the main body may include: a light source unit for providing light; and a light processing unit for processing light, and the light processing unit may include: a beam splitter for splitting the light of the light source unit into a first beam serving as a reference beam and a second beam serving as a sample beam; and a scanner provided at the rear of the beam splitter so as to vary the angle of the second beam.

7 Claims, 7 Drawing Sheets

(56) References Cited

U.S. PATENT DOCUMENTS

2012/0194661 A1* 8/2012 Lee .................. A61B 1/04
                                              348/68
2015/0313467 A1* 11/2015 Sakai ............... A61B 3/102
                                              351/208

* cited by examiner

ENDOSCOPE, HANDPIECE OF ENDOSCOPE, CALIBRATION METHOD THEREFOR, AND METHOD FOR USING THE SAME

BACKGROUND

1. Technical Field

The present disclosure relates to an endoscope, and in particular, to an endoscope which can be used in various manners, implement a high resolution, and perform a diagnosis without making a large incision on the human body, a hand piece of the endoscope, a calibration method therefor, and a method for using the same.

2. Related Art

An endoscope refers to a device which enables a user to observe various parts such as the alimentary canal, thoracic cavity, and joint of the human body with the naked eye, without making an incision. Among various endoscopes, only a device for observing an alimentary canal may be referred to as an endoscope. However, the present invention is not limited thereto, but all types of devices for observing the internal organs of the human body may be referred to as endoscopes. In particular, the present invention provides an endoscope which can be properly used for a part into which a needle is inserted. For example, the endoscope can be used in various parts such as the chest cavity, the abdominal cavity, a joint, the bladder, the spine, and the brain of the human body.

Although a conventional endoscope was developed to conduct a non-invasive treatment, a part of the endoscope, which is inserted into the human body, has a relatively large size. Due to such a problem, the endoscope may leave a large scar in the chest, abdomen, or joint of a patient, and cause pain. Furthermore, when the endoscope is inserted into the alimentary canal, the endoscope may cause the patient pain. Due to such a problem, although the endoscope was aimed at non-invasive treatment, an endoscope treatment is performed after the patent is induced to sleep.

Considering such a problem, Korean Patent Publication No. 10-2013-0080940 has disclosed a scanner-free single fiber micro-endoscope and an imaging method using the same. Since the endoscope is implemented only with a piece of optical fiber, a patient can receive an endoscope treatment without a pain.

According to the related art, the scanner-free single fiber micro-endoscope employs a sample beam and a reference beam, and acquires an interference image of the sample beam and the reference beam. When the image is acquired, a first distortion of the image occurs due to the optical fiber while light propagates to an object plane (OP) from an image plane (IP), and a second distortion of the image occurs while the light returns to the IP from the OP. The related art provides a method for acquiring a high-quality image by overcoming the distortions. Between the above-described distortions, the first distortion may be removed through a process of adding up a plurality of repeated images, and the second distortion may be removed through a process of obtaining a transmission matrix by passing light at various angles and recovering a distorted image through the transmission matrix.

In the technology according to the related art, however, when the path length and shape of the optical fiber from the IP to the OP are changed, the previous transmission matrix cannot be applied. Thus, the image cannot be recovered. In other words, when the endoscope inserted into the human body is bent to observe a diseased part, the transmission matrix of the optical fiber may be changed by the deformation of the endoscope, and the image cannot be recovered. Thus, the endoscope could not be applied for the use of an endoscope. Furthermore, since an area from which an image can be obtained is limited to a small range, there are difficulties in applying the endoscope to a wide range.

SUMMARY

Various embodiments are directed to an endoscope which can perform an endoscope treatment without causing pain to a patient and provide a high-resolution image, and can be actually applied.

In an embodiment, there is provided an endoscope including a hand piece held by a hand and a main body connected to the hand piece. The hand piece may include a high-strength bar having an optical path providing unit formed therein, the main body may include: a light source unit for providing light; and a light processing unit for processing light, and the light processing unit may include: a beam splitter for splitting the light of the light source unit into a first beam serving as a reference beam and a second beam serving as a sample beam; and a scanner provided at the rear of the beam splitter so as to vary the angle of the second beam. When the endoscope is applied, a doctor may perform an endoscope treatment or laparoscope treatment in the form of a needle having almost no diameter.

The optical path providing unit may include one of a GRIN (GRaded-INdex) bar lens, a piece of optical fiber, and an optical fiber bundle. The first beam may be connected to the hand piece through a single mode optical fiber, and the second beam may be connected to the hand piece through a multi-mode optical fiber. Thus, patterns may be allocated to laser beams in order to perform analysis.

The light source unit may include an RGB laser source and a dichroic mirror for combining RGB lights. Furthermore, a switching mirror may be provided at the rear of the scanner, and a calibration port may be provided at the rear of the switching mirror so as to selectively acquire a transmission matrix of the bar.

In another embodiment, an endoscope may include a main body and a hand piece held by a user. The hand piece may include an LED light source for observing a wide area, and the main body may include a laser light source for observing a narrow area. Thus, a wide area image and a narrow area image can be acquired at the same time.

In another embodiment, there is provided a hand piece of an endoscope, which is held by a user to perform examination. The hand piece may include: a bar inserted into a human body, and including an optical path providing unit formed in a high-strength external case; a beam splitter for splitting an optical path of first and second laser beams provided from outside; an LED light source; and a switching mirror provided at an optical path of the first laser beam and an optical path of the LED light source, and selectively providing the first laser beam or light of the LED light source to the bar. According to the hand piece, a structure on which light is incident may be connected to the hand piece in a state where large and heavy parts are arranged in another device. Thus, a doctor may conveniently perform examine while having the hand piece in the hand.

The hand piece may further include: an imaging device provided in the downstream of the optical path of the beam splitter so as to take an image; and a display for displaying the image formed in the imaging device.

In another embodiment, a calibration method for an endoscope may include: mounting a bar in a main body of the endoscope, the bar having an optical path providing unit;

obtaining a sample beam by passing a part of laser through the bar, obtaining a reference beam by not passing the other part of the laser through the bar, and passing the sample beam and the reference beam into the hand piece of the endoscope; acquiring an interference image of the reference beam and the sample beam through the hand piece; and obtaining a transmission matrix of the bar by referring to the interference image information. According to the calibration method, the transmission matrix of the bar can be conveniently obtained without a separate attempt.

In another embodiment, a method for using an endoscope may include: irradiating LED light; acquiring an image of a wide area using the LED light; irradiating laser; and acquiring an expanded image of a narrow area using the laser. According to the method, a wide area and a narrow area can be observed together, and the endoscope can be more conveniently used during a doctor's examination.

DETAILED DESCRIPTION

Figure 1:
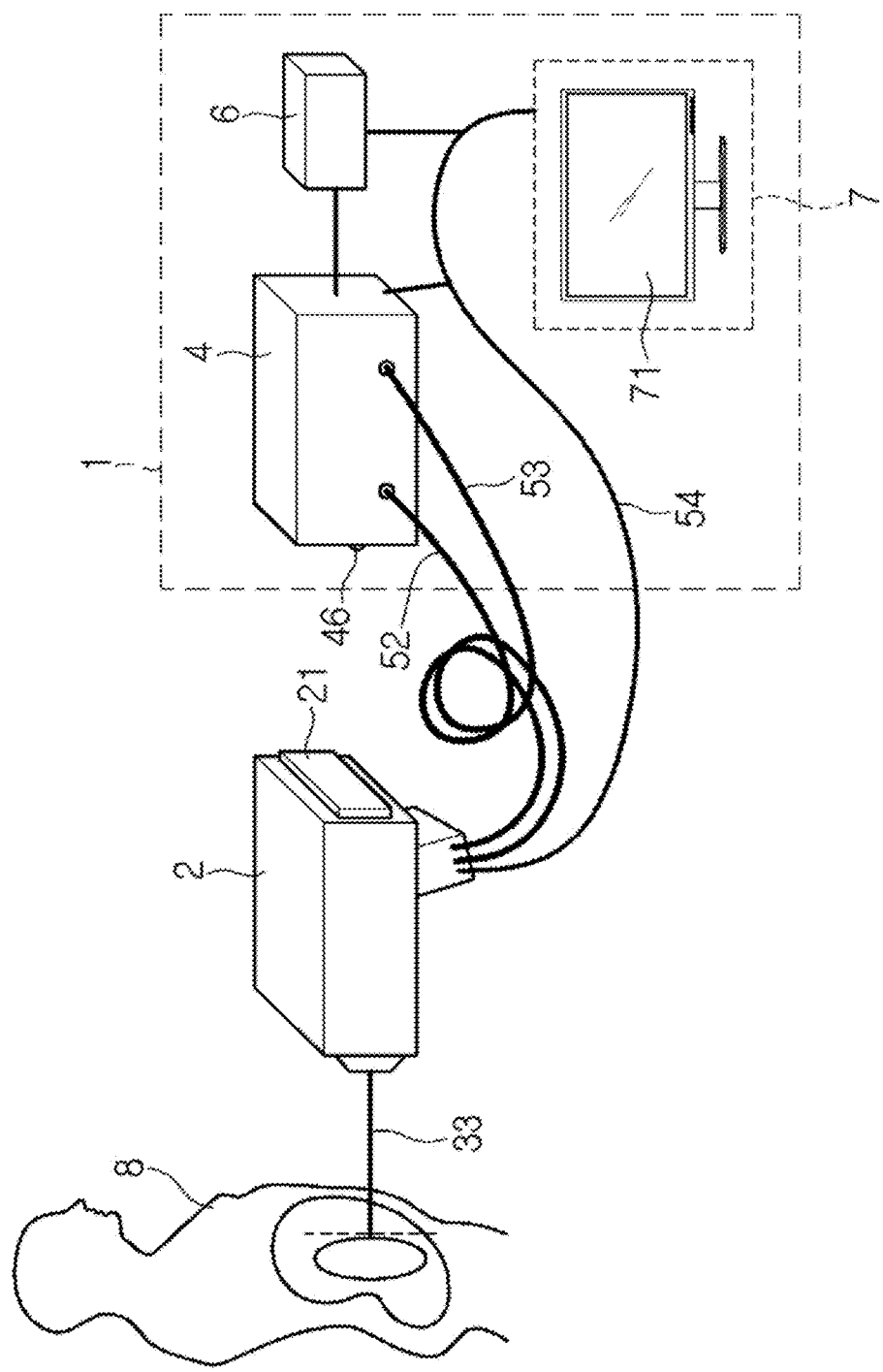
FIG. 1 is a diagram illustrating the configuration of an endoscope according to an embodiment of the present invention.

Exemplary embodiments will be described below in more detail with reference to the accompanying drawings. The disclosure may, however, be embodied in different forms and should not be constructed as limited to the embodiments set forth herein. Rather, these embodiments are provided so that this disclosure will be thorough and complete, and will fully convey the scope of the disclosure to those skilled in the art. Throughout the disclosure, like reference numerals refer to like parts throughout the various figures and embodiments of the disclosure.

The drawings are schematic drawings, and the specific shapes or scales of components can be changed unless referred specifically.

FIG. 1 is a diagram illustrating the configuration of an endoscope according to an embodiment of the present invention.

Referring to FIG. 1, the endoscope may include a hand piece 2 and a main body 1. The hand piece 2 may be held by a doctor so as to be applied to a patient 8, and the main body 1 may exchange light and data with the hand piece 2.

The hand piece 2 may have a bar 33 provided at an end thereof. The bar 33 may include a hollow needle formed of high-strength stainless steel and an optical path providing unit formed in the hollow needle so as to provide an optical path. The optical path providing unit may be formed of glass. The optical path providing unit may include a bar lens, an optical fiber bundle, or a piece of optical fiber. The bar lens may include a GRIN (GRaded-INdex) bar lens. Since the optical path providing unit can have a thickness of several tens to several hundreds of micrometers, the bar 33 may have a thickness corresponding to an injection needle which is generally used. An end of the bar 33 at the hand piece 2 may be set to an image plane (IP), and the other end of the bar 33 at the patient 8 may be set to an object plane (OP).

The hand piece 2 may include a display 21 through which a doctor can observe an image acquired through the endoscope.

The main body 1 may include a light source unit 6 for providing light, a light processing unit 4 for processing light provided from the light source unit 6, and a controller 7 for controlling overall operations of the endoscope. The controller 7 may include a display 71 which has a larger size than the display 21 of the hand piece 2 and through which a high-resolution image can be observed. The light source unit 6 and the light processing unit 4 may be provided as a single device. The controller 7 and the hand piece 2 may include a user interface (UI).

The operation of the endoscope will be described.

First, the light processing unit 4 may include a calibration port 46. The calibration port 46 on which the bar 33 is mounted may acquire a transmission matrix of the bar 33. The bar 33 of which the transmission matrix is acquired may be mounted on the hand piece 2. The process of acquiring the transmission matrix will be described below in detail. Furthermore, the bar 33 of which the transmission matrix is acquired may be provided as a needle formed of stainless steel. Thus, since the bar 33 is not bent, the optical path is not changed. Therefore, the transmission matrix which has been measured once can be continuously used, thereby solving the problem that occurs when the optical path is changed in the conventional endoscope.

When a doctor examines a patient, the light generated from the light source unit 6 may be split and provided to two paths. More specifically, the light may include a first beam which is provided to the bar 33 and a second beam which is not provided to the bar 33. The first beam may be provided to the hand piece 2 through a multi-mode optical fiber 52, and the second beam may be provided the hand piece 2 through a single-mode optical fiber 53.

The first beam provided to the hand piece 2 may illuminate the internal organs of the patient through the bar 33 and then reflect and return. The first beam may be referred to as a sample beam. The second beam which is provided to the hand piece 2 but not provided to the bar 33 may cause interference with the sample beam. The second beam may be referred to as a reference beam. An interference image obtained through the interference between the reference beam and the sample beam may be transmitted to the controller 7, and then processed into an image through an image processing operation.

The controller 7 may apply a digital holographic algorithm to the interference image, and calculate the magnitude and phase of the sample beam. Furthermore, the controller 7 may use a previously known transmission matrix of the bar 33, and recover the original image through a process of adding up a plurality of images. The image processing process may include a method disclosed in Korean Patent Laid-open Publication No. 10-2013-0080940. Within a necessary range, the image processing process may be included in the descriptions of the present embodiment. Furthermore, other image processing methods may be applied.

The obtained image may be displayed on the display 71 of the controller 7, or transmitted to the hand piece 2 and displayed on the display 21 of the hand piece 2.

Hereafter, the detailed configuration of the endoscope will be described as follows.

Figure 2:
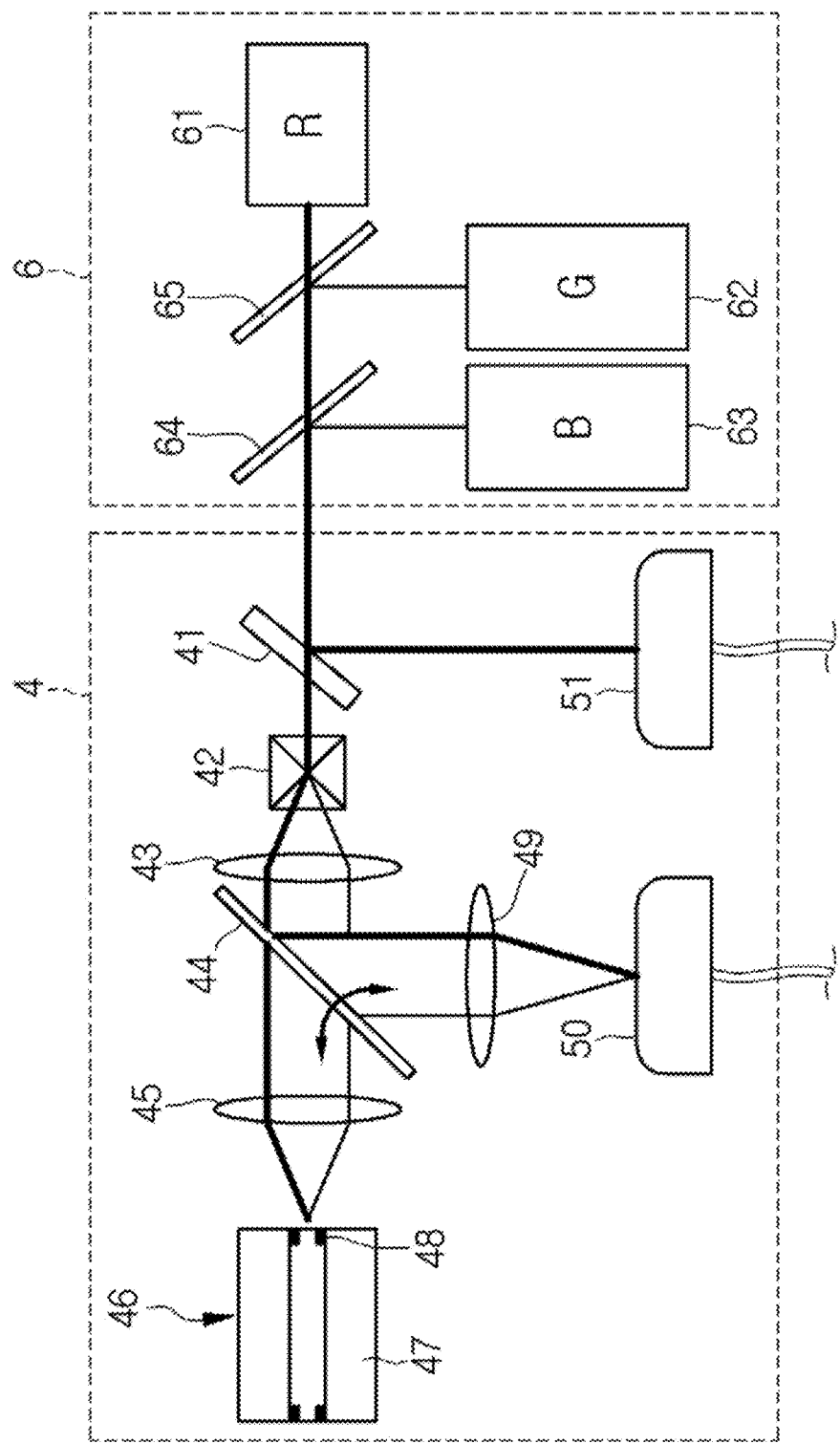
FIG. 2 is a block diagram for describing the configuration of a light source unit and a light processing unit.

FIG. 2 is a block diagram for describing the configuration of the light source unit and the light processing unit.

Referring to FIG. 2, the light source unit 6 may include laser sources 61 to 63 and first and second dichroic mirrors 65 and 64. The laser sources 61 to 63 may irradiate RGB lasers, and the first and second dichroic mirrors 65 and 64 may combine the lasers irradiated from the laser sources. As the RGB lasers are irradiated, a color image can be finally realized. Instead of the RGB lasers, a single laser may be provided.

The light of the light source unit 6 may be provided to the light processing unit 4. The light incident on the light processing unit 4 may be split by a second beam splitter 41. One may be incident as the second beam on a single mode fiber coupler (SMFC) 53 and serve as the reference beam, and the other one may be incident as the first beam on a multi-mode fiber coupler (MMFC) through a scanner 42, a first lens 43, a first switching mirror 44, and a second lens 49.

The scanner 42 may include an X-Y two-axis galvano scanner. However, the scanner 42 is not limited thereto, but may include any scanners as long as the scanners can adjust light at various angles. For example, devices using diffraction, such as AOMs (Acousto-Optic Modulators) and SLM (Spatial Light Modulator), may be used as the scanner. The SLM may include a DMD (Digital Micro-mirror Device). The scanner 42 is a relatively large device which performs a plurality of variable operations. The scanner 42 may be provided in the main body 1 which is installed in a stationary state, instead of the hand piece 2. Thus, the hand piece can be reduced to such a size that can be held by the hand, and the scanner 42 does not cause a breakdown during the operation of the endoscope or does not abnormally operate due to an external impact.

The first switching mirror 44 may be provided at the rear of the first lens 43 on the optical path. The switching mirror may include a flip mirror, and reflect or pass light. When the first switching mirror 44 reflects light, it may indicate the operational mode of the endoscope. Specifically, when the first switching mirror 44 reflects light passing through the first lens 43, the reflected light may be incident on the second lens 49. The light passing through the second lens 49 may become the first beam to be incident on the multi-mode fiber coupler 50, and serve as the sample beam afterwards. On the other hand, when the first switching mirror 44 passes light, it may indicate the calibration mode of the endoscope. Specifically, when the first switching mirror 44 passes light, the light may be incident on a third lens 45 and irradiated to the calibration port 46. The calibration port 46, on which the bar 33 is mounted, may measure the transmission matrix of the bar 33. The calibration mode of the endoscope will be described below. The calibration port 46 may include a port housing 47 into which the bar 33 is inserted and a support structure 48 which supports the bar 33 such that the bar 33 is not moved.

The light incident on the multi-mode fiber coupler 50 may be supplied to the hand piece 2 through the multi-mode optical fiber 52, and the light incident on the single mode fiber coupler 51 may be supplied to the hand piece 2 through the single mode optical fiber 53. The single mode optical fiber 53 may include a core layer of which the diameter is several micrometers. Since light passing through the single mode optical fiber 53 exhibits a Gaussian distribution, the light may be used as the reference beam. The multi-mode optical fiber 52 may include a core layer of which the diameter is several tens to several hundreds of micrometers, and light passing through the multi-mode optical fiber 52 may have predetermined patterns or speckles formed therein. As the patterns are reflected from the OP in a unique form, an image of the OP may be acquired, and used as the sample beam. The image distortion caused by the speckles may be removed through a laser speckle imaging method. That is, the image distortion may be removed through a process of adding the image many times.

Figure 3:
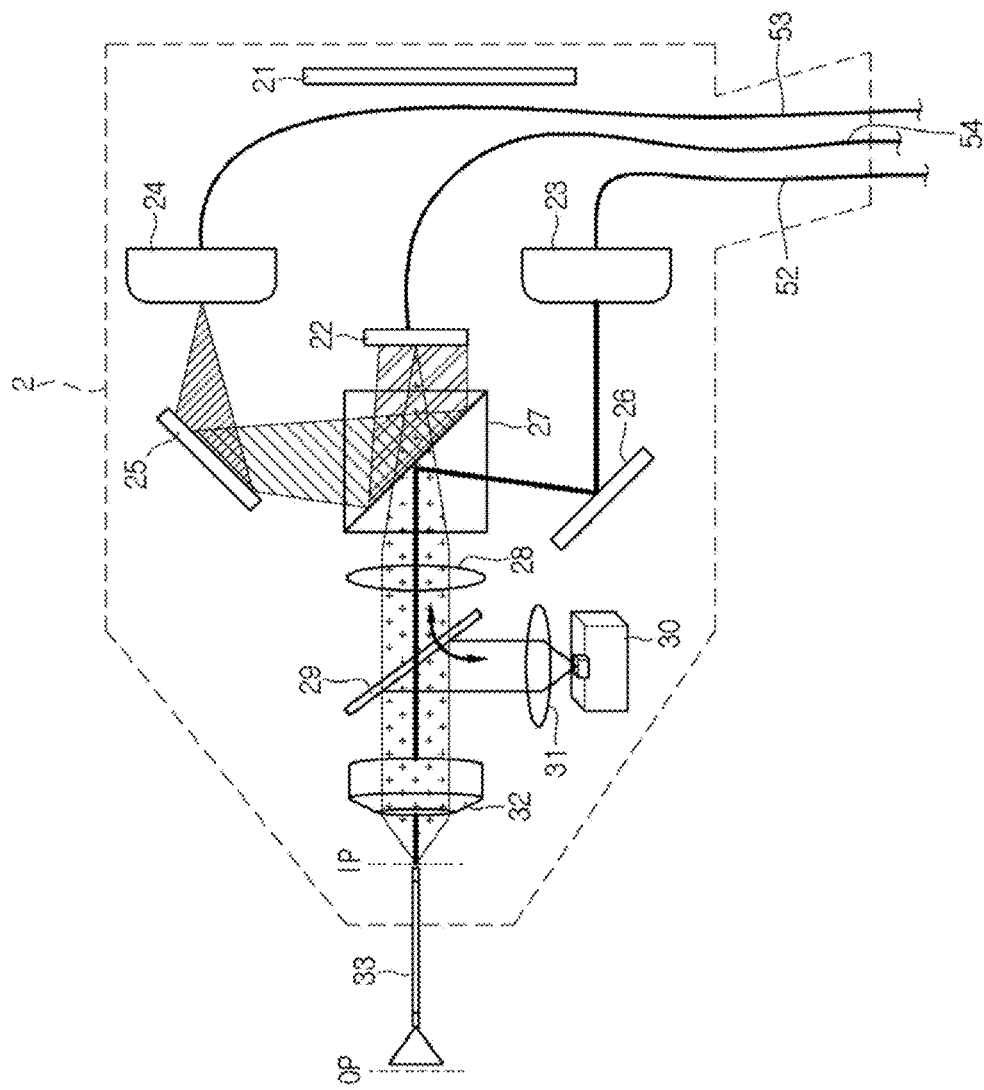
FIG. 3 is a block diagram for describing the configuration of a hand piece in detail.

FIG. 3 is a block diagram for describing the configuration of the hand piece in detail.

Referring to FIG. 3, the single mode optical fiber 53 may be connected to a single mode connector 24 to emit the second beam, and the light may be reflected through a first fixed mirror 25 and incident on a first beam splitter 27. Then, the light may be reflected at the first beam splitter 27 and incident as the reference beam on an imaging device 22, for example, a CCD. The multi-mode optical fiber 52 may be connected to a multi-mode connector 23 to emit the first beam, and the light may be reflected at a second fixed mirror 26 and incident on the first beam splitter 27. Then, the light may be reflected at the first beam splitter 27 and incident on the bar 33 through a fourth lens 28 and an object lens 32. The light may be emitted through the optical path providing unit of the bar 33, and reflected from an internal organ or object. Then, the light may return as a sample beam through the bar 33. The sample beam may be incident on the imaging device 22 through the first beam splitter 27 after passing through the object lens 32 and the fourth lens 28 in the reverse order. The light incident on the imaging device 22 may be displayed on the display 21, or transmitted to the main body 1 and displayed on the display 71 of the main body 1.

Through the above-described process, the reference beam and the sample beam may be incident together. Thus, the reference beam and the sample beam may cause interference, and the interference may be analyzed to obtain an image.

Between the fourth lens 28 and the object lens 32, a second switching mirror 29 and an LED light source 30 may be provided. The second switching mirror 29 may include a flip mirror, and switch the optical path between the fourth lens 28 and the object lens 32 such that LED light of the LED light source 30 is reflected at the second switching mirror 29 through a fifth lens 31 and incident on the object lens 32. The LED light may be reflected from an internal organ through the optical path providing unit of the bar 33, and incident on the imaging device 22 after passing through the bar 33, the object lens 32, the second switching mirror 29, the fourth lens 28, and the first beam splitter 27 in the reverse order.

According to the second switching mirror 29, the hand piece 2 may provide two kinds of observation modes. The first observation mode is a wide area mode. In the wide area mode, LED light may be used to acquire a relatively wide area of image. In this case, an image of an internal organ area corresponding to several centimeters or several tens of centimeters can be acquired. The second observation mode is a narrow area mode. In the narrow area mode, laser light may be used to acquire a relatively narrow area of image. In this case, an image of an internal organ area corresponding to several micrometers or several tens of micrometers can be acquired. The difference between the observation modes is based on the aberrations of the lenses, the difference between lights, and the suitability of the light processing method.

When a doctor uses the endoscope in the field, the doctor may penetrate the skin of a patient through minimum invasion, insert the bar 33 into the skin, and examine a wide area using the LED light source 30 in the wide area mode. Then, when more accurate examination is required, the doctor may examine a narrow area using the light source unit 6 in the narrow area mode.

Hereafter, the operation of the endoscope for each mode will be described in detail.

First, the process of acquiring the transmission matrix of the bar 33 will be described. This mode may be referred to as the calibration mode of the endoscope. The bar 33 may be mounted on the calibration port 46. At this time, the bar 33 may be already mounted on the hand piece 2. The switching state of the second switching mirror 29 may be set to an off state.

The first switching mirror 44 may be set in an off state, and cause light passing through the first lens 43 to propagate toward the third lens 45. Then, the light incident on the light processing unit 4 from the light source unit 6 may be partially reflected at the second beam splitter 41 and incident as the reference beam on the single mode fiber coupler 51. However, the light passing through the second beam splitter 41 may be incident on the bar 33 through the scanner 42, the first lens 43, and the third lens 45. The light passing through the bar 33 may be incident on the hand piece 2, and reach the object lens 32, the fourth lens 28, and the first beam splitter 27. As described above, the bar 33 may be mounted on the calibration port 46 in a state where the bar 33 sticks in the hand piece 2. At this time, the scanner 42 may adjust light at various angles. The light passing through the bar 33 may become a sample beam.

The light incident on the single mode fiber coupler 51 may be passed as the reference beam through the single mode optical fiber 53, and incident on the imaging device 22 through the single mode connector 24, the first fixed mirror 25, and the first beam splitter 27.

The light reaching the imaging device 22 may include the reference beam and the sample beam. The interference image information obtained through the imaging device 22 may be transmitted to the controller 7 of the main body 1, and the controller 7 may calculate the transmission matrix of the bar 33. At this time, as the scanner 42 irradiates laser at different angles, the transmission matrix may be obtained as various cases.

The transmission matrix may differ depending on the area or magnification of the image acquired through the endoscope. For example, a desired focal distance may be set, and an image may be acquired at the set focal distance. Furthermore, known transmission matrixes may be stored in the controller 7, and the bar 33 of which a specific transmission matrix is known may be applied to the hand piece 2. Then, the operation of the endoscope may be performed.

The operation mode of the endoscope will be described in detail.

A doctor may insert the bar 33 into the skin of a patient through minimum invasion. At this time, the wide area mode may be used for a relatively wide area, and the narrow area mode may be used for a narrow area. First, the wide area mode of the operation mode of the endoscope will be described.

When the wide mode is applied, the light processing unit 4 and the light source unit 6 using laser may be turned off, and a process of pulling the optical fiber connector may not be used. The second switching mirror 29 may be turned on to reflect the light of the LED light source 30 through the second switching mirror 29, and the reflected light may be incident on the object lens 32. The light may be focused through the object lens 32 and incident on the bar 33. Then, the LED light passing through the optical path providing unit of the bar 33 may be reflected and returned to the bar 33. Then, the light may be passed through the object lens 32 and the second switching mirror 29 in the reverse order, and incident on the imaging device 22 through the fourth lens 28 and the first beam splitter 27.

The doctor may examine an internal organ in the range of several square centimeters to several tens of square centimeters, while watching the display 21 of the hand piece or the display 71 of the main body. The wide area mode of the endoscope can be reliably performed through the operation of the controller 7 of the hand piece 2.

During the wide area mode, a specific diseased part might need to be expanded on a micro basis so as to be examined or need to be observed on a cell basis. In this case, the narrow area mode may be performed.

When the narrow area mode is applied, the second switching mirror 29 may be turned off and the light emitted from the LED light source 30 may not be incident on the bar 33, but the first switching mirror 44 may be turned on to reflect the light coming from the first lens 43 onto the second lens 49. The light source unit 6 may start operation to irradiate RGB lasers. The light irradiated from the light source unit 6 may be partially reflected at the second beam splitter 41 and incident as the second beam on the single mode fiber coupler 51. However, the light passing through the second beam splitter 41 may be passed through the scanner 42 and the first lens 43, reflected at the first switching mirror 44, and incident on the multi-mode fiber coupler 50 through the second lens 49. At this time, the scanner 42 may adjust the light at various angles.

The light incident on the single mode fiber coupler 51 may be incident on the first beam splitter 27 through the single mode optical fiber 53, the single mode connector 24, and the first fixed mirror 25, reflected as the reference beam at the first beam splitter 27, and then incident on the imaging device 22.

The light incident on the multi-mode fiber coupler 50 may be incident on the first beam splitter 27 through the multi-mode optical fiber 52, the multi-mode connector 23, and the second fixed mirror 26, and then reflected. The reflected first beam may be focused through the fourth lens 28 and the object lens 32, and incident on the bar 33. The first beam may be emitted through the bar 33, reflected from an internal organ of the patient, and returned as a sample beam to the bar 33. Then, the sample beam may pass through the object lens 32, the fourth lens 28, and the first beam splitter 27 in the reverse order and reach the imaging device 22.

Through the above-described process, an interference image of the reference beam and the sample beam may be taken through the imaging device 22, and the taken image may be transmitted to the main body 1 through a data line 54. The transmitted interference image may be processed through an inverse matrix of the transmission matrix so as to remove distortion in the optical path providing unit of the bar 33. Through a process of linearly adding up the plurality of images of which distortions are removed, distortion caused by speckles existing in the multi-mode optical fiber may be removed to recover the image into an original clear image. The recovered image may be checked through the display 71 of the main body 1. At this time, since the information of the recovered image can be displayed by the unit of micrometer, examination can be performed on a cell basis. Furthermore, the magnification range may be differently set, and a transmission matrix based on the magnification range may be provided to perform examination on a tissue basis.

When the hand piece 2 has information on the transmission matrix, an expanded image of a narrow area can be directly observed through the hand piece 2, and an image which is processed and finally obtained through the controller 7 may be transmitted to the hand piece 2 such that the expanded image of the narrow area can be indirectly observed.

Figure 4:
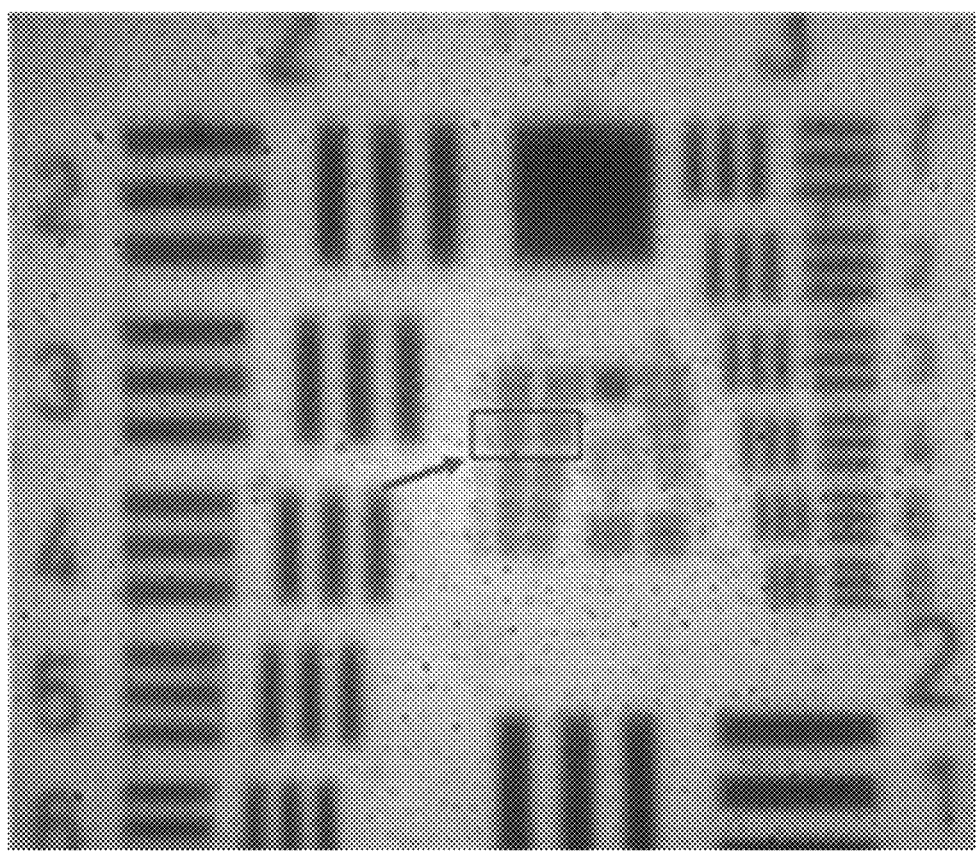
FIG. 4 is a photograph taken in the wide area mode.
Figure 5:
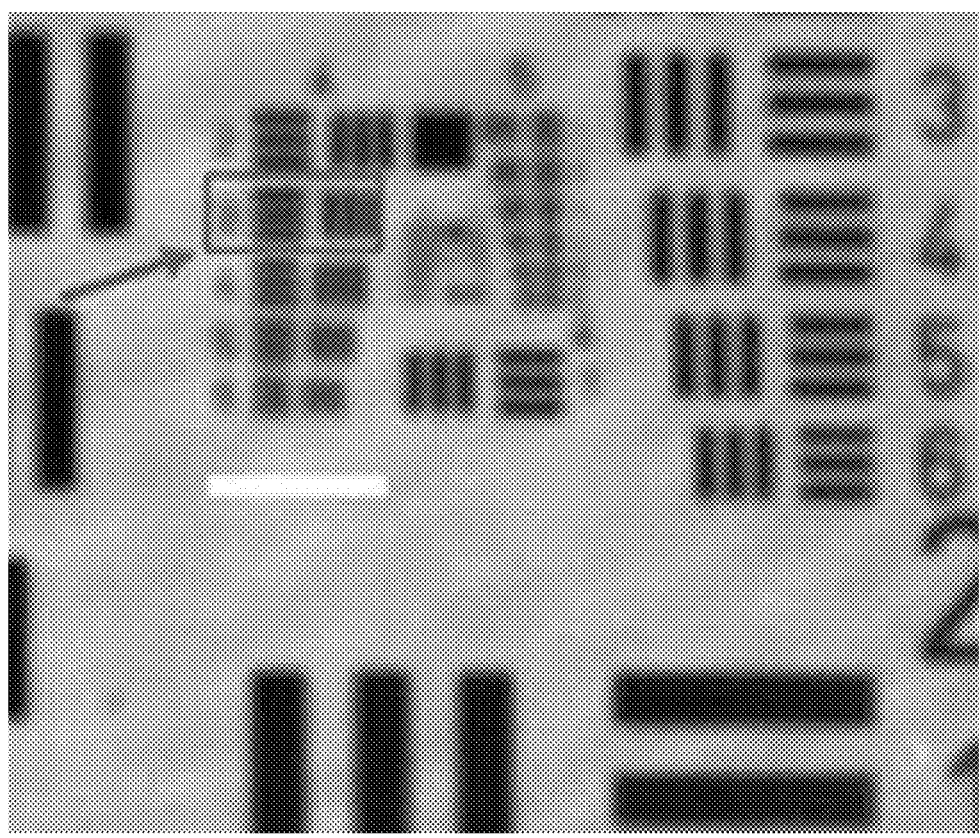
FIG. 5 is a photograph taken in the narrow area mode.

FIG. 4 is a photograph taken in the wide area mode, and FIG. 5 is a photograph taken in the narrow area mode. FIGS. 4 and 5 illustrate the same area. The wide area mode has a limitation in examination. In the narrow area mode, however, a user can examine a more minute part. However, in the narrow area mode, the user may have difficulties in observing a wide area.

Hereafter, a method for using the endoscope according to the embodiment of the present invention will be described. Since the method is based on the configuration of the endoscope, the following descriptions will be made by referring to the configuration of the endoscope.

Figure 6:
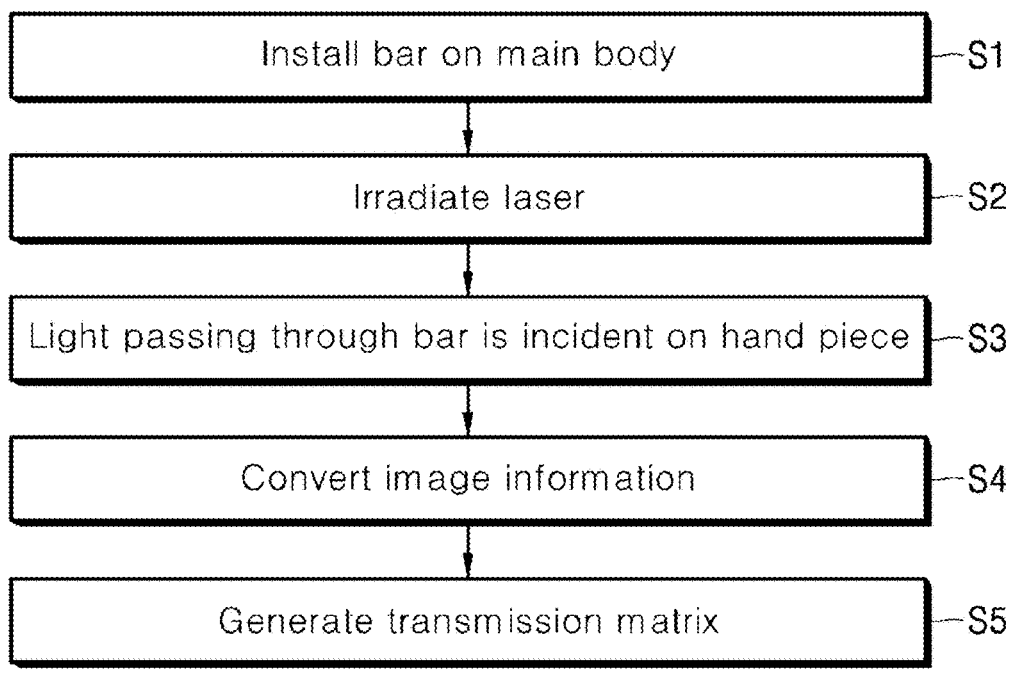
FIG. 6 is a flowchart for describing the calibration method of the endoscope according to the embodiment of the present invention.

FIG. 6 is a flowchart for describing the calibration method of the endoscope according to the embodiment of the present invention.

Referring to FIG. 6, the bar 33 may be mounted on the main body of the endoscope at step S1. At this time, the bar may have the optical path providing unit formed therein. Laser may be irradiated onto the bar at step S2. The laser may be incident as a sample beam on the hand piece through the bar, at step S3. At this time, at least a part of the laser may not be passed through the bar, but incident as a reference beam on the hand piece. The hand piece may convert an interference image of the reference beam and the sample beam into digital information at step S4, and generate a transmission matrix of the bar by referring to the interference image information at step S5.

Figure 7:
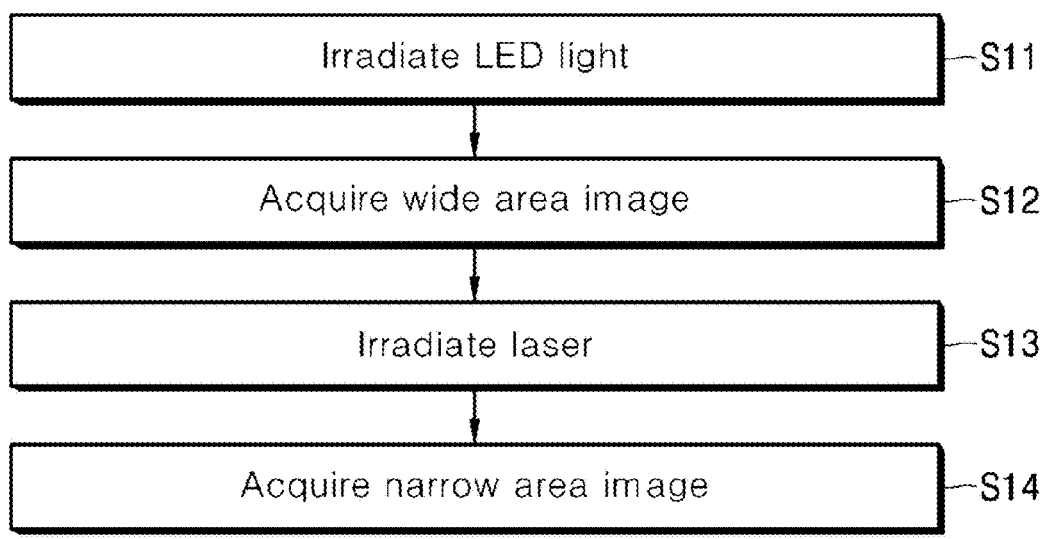
FIG. 7 is a flowchart for describing a method of using the endoscope according to the embodiment of the present invention.

FIG. 7 is a flowchart for describing a method of using the endoscope according to the embodiment of the present invention.

Referring to FIG. 7, LED light may be irradiated at step S11, and an image of a wide area may be acquired through the LED light at step S12. A doctor may perform examination while watching the wide area image. When accurate diagnosis is requested after the doctor determines a diseased part through the wide area image, laser may be irradiated at step S13, and an expanded image of a narrow area may be acquired through the laser at step S14.

According to the above-described method, more accurate examination can be performed through one diagnosis.

According to the embodiments of the present invention, laser may be used to realize a realistically expanded image, the essential elements may be implemented in the hand piece, and the other structures may be provided in the main body such that a doctor can hold the hand piece to perform examination. Thus, the doctor can minimize a side effect through minimum invasion, thereby performing an endoscope treatment without causing a patient pain. Furthermore, since low-resolution and high-resolution images can be implemented together, a wide area and a narrow area can be sequentially observed. Thus, a diseased part can be easily observed. Therefore, the endoscope can be applied to the industry, thereby contributing to health promotion of the human beings.

While various embodiments have been described above, it will be understood to those skilled in the art that the embodiments described are by way of example only. Accordingly, the disclosure described herein should not be limited based on the described embodiments.

What is claimed is:

1. An endoscope, comprising:
a hand piece configured to be held by a hand, wherein the hand piece comprises:
   a high-strength bar having an optical path providing unit formed therein;
   a hand piece light source configured to provide a light for a wide area mode of the endoscope; and
   a first switching mirror configured to reflect the light provided from the hand piece light source to the optical path in the high-strength bar; and
a main body connected to the hand piece, wherein the main body comprises:
   a main body light source unit configured to provide a light for a narrow area mode of the endoscope;
   a light processing unit for processing the light for the narrow area mode, wherein the light processing unit comprises:
      a beam splitter for splitting the light for the narrow area mode into a first beam serving as a reference beam and a second beam serving as a sample beam; and
      a scanner provided at the rear of the beam splitter so as to vary the angle of the second beam; and
      a second switching mirror configured to reflect the second beam split by the beam splitter so as to provide the second beam to the optical path in the high-strength bar; and
wherein, when the wide area mode is applied, the first switching mirror is turned on and the main body light source unit is turned off,
wherein, when the narrow area mode is applied, the first switching mirror is turned off and the second switching mirror is turned on and the main body light source is turned on,
wherein the hand piece further comprises an imaging device configured to take an interference image using the first beam and the second beam, and to take an image using the light for wide area mode, and
wherein the optical path providing unit of the high-strength bar is configured to transmit the light for the wide area mode, the first beam, and the second beam through the high-strength bar.

2. The endoscope of claim 1, wherein the optical path providing unit comprises one of a GRIN (GRaded-INdex) bar lens, a piece of optical fiber, or an optical fiber bundle.

3. The endoscope of claim 1, wherein the first beam is transmitted to the hand piece through a single mode optical fiber, and the second beam is transmitted to the hand piece through a multi-mode optical fiber.

4. The endoscope of claim 1, wherein the main body light source unit comprises an RGB laser source and a dichroic mirror for combining RGB lights.

5. The endoscope of claim 1, wherein the second switching mirror is provided at the rear of the scanner, and
a calibration port is provided at the rear of the second switching mirror so as to selectively acquire a transmission matrix of the bar.

6. A hand piece of an endoscope configured to be held by a user to perform examination, the hand piece comprises:
a bar configured to be inserted into a human body, wherein the bar comprises:
   an optical path providing unit formed in a high-strength external case;
a beam splitter for splitting an optical path of a first beam and an optical path of a second laser beam provided from outside, wherein the first beam and the second beam are for a narrow area mode of the endoscope;

a hand piece light source configured to provide a light for a wide area mode of the endoscope;

an imaging device configured to take an interference image using the first beam and the second beam, and to take an image using the light for wide area mode; and a switching mirror provided at an optical path of the first beam and an optical path of the light for the wide area mode wherein the switching mirror reflects the light provided from the hand piece light source to the optical path of the light for the wide area mode, by being turned on when the wide area mode is applied, and wherein the switching mirror passes the first beam to the optical path of the first beam, by being turned off when the narrow mode is applied.

7. The hand piece of claim 6, further comprising:

a display for displaying the image formed in the imaging device.

* * * * *